United States Patent [19]
Healey

[11] Patent Number: 4,721,109
[45] Date of Patent: Jan. 26, 1988

[54] TEMPORARY ANASTOMOTIC DEVICE

[76] Inventor: Maureen A. Healey, 98 Oceanside Dr., P.O. Box 374, Scituate, Mass. 02066

[21] Appl. No.: 849,287

[22] Filed: Apr. 8, 1986

[51] Int. Cl.$^4$ .................. A61B 17/04; A61M 29/00; A61F 2/04

[52] U.S. Cl. .................. 128/334 R; 604/96; 623/12

[58] Field of Search ............ 128/334 R, 344; 604/96; 623/1, 12

[56] References Cited

U.S. PATENT DOCUMENTS

| | | | |
|---|---|---|---|
| 2,836,181 | 5/1958 | Tapp | 128/334 R |
| 3,154,077 | 10/1964 | Cannon | 128/344 |
| 3,435,824 | 4/1969 | Gamponia | 128/334 R |
| 3,435,826 | 4/1969 | Fogarty | 128/344 |
| 3,516,408 | 6/1970 | Montani | 128/334 R |

FOREIGN PATENT DOCUMENTS 512456 9/1939 United Kingdom .............. 128/344

Primary Examiner—Richard C. Pinkham
Assistant Examiner—Gary Jackson
Attorney, Agent, or Firm—John P. McGonagle

[57] ABSTRACT

An anastomotic device for temporary installation in a damaged blood vessel, having a generally tube-like shape, and whose purpose is to maintain blood flow within the blood vessel while substantially halting bleeding. The device is so inserted into the damaged blood vessel that it reconnects and reforms the blood vessel through the damaged area. The device contains an enclosed chamber, inflatable from an external source, concentric about an inner cylinder with open ends. The inner cylinder maintains blood flow while the inflated air chamber causes the device to fit snugly enough within the blood vessel to halt external bleeding.

3 Claims, 8 Drawing Figures

TEMPORARY ANASTOMOTIC DEVICE

BACKGROUND OF THE INVENTION

This invention relates to anastomotic devices and more particularly to a temporary anastomotic device for controlling bleeding from damaged or severed blood vessels and restoring a more normal pattern of circulation.

Trauma is a national epidemic which has only recently been recognized as a major medical problem. In 1982, trauma was the third leading cause of death in the United States following cardiovascular disease and cancer. Morbidity from trauma is estimated at 400,000 in the United States. By plotting death rates from trauma in a frequency over time after injury relationship, a trimodal distribution may be observed. The first peak, characterized as "immediate deaths", represents people who die very soon after an injury. Invariably, these deaths are caused by lacerations of the brain, the brain stem, the spinal cord, the heart, or one of the major blood vessels. The second peak, characterized as "early deaths", represents people who die within the first few hours after an injury. These deaths are usually caused by major internal hemorrhages of the head, the respiratory system, the abdominal organs, or by multiple lesser injuries resulting in severe blood loss. The third peak, characterized as "late deaths", represents people who die days or weeks after an injury, usually from complications resulting from the types of injuries described above. What readily becomes apparent from this type of analysis is that hemorrhage is one of the leading causes of trauma death.

SUMMARY OF THE INVENTION

The present invention is directed to reducing hemorrhaging in people suffering from trauma. The invention is comprised of a tube-like device which acts as a temporary anastomotic device and can be inserted into both ends of a severed or partially severed blood vessel to decrease and control bleeding at the accident scene.

The anastomotic device is temporary and would not replace arterial grafts or surgical anastomotic devices. It can be inserted by a guide, where needed, and does not require sutures. The tempoary anastomotic device is so inserted into a damaged blood vessel that it reconnects and reforms the blood vessel in and through the damaged area. The device contains an enclosed inflatable chamber concentric about an inner cyclinder with open ends. The inner cyclinder maintains blood vessel flow while the inflated chamber causes the device to fit the blood vessel snugly enough that bleeding from the blood vessel is halted, or at least substantially reduced.

The temporary anastomotic device would usually be used at the scene of an accident by paramedics trained to perform invasive resuscitative techniques. However, the invention may also be useful to the emergency room doctor, e.g., for patients with rupture of the abdominal aorta. The profuse hemorrhage accompanying this type of rupture leaves the patient with profound hypovolemia. Immediate insertion of the temporary anastomotic device into the aorta will ensure a continuous blood supply to the lower part of the body, thereby decreasing blood loss and improving coronary and cerebal circulation.

Prompt treatment of patients with injuries resulting in hemorrhage will decrease morbidity and mortality. Decreasing the morbidity and mortality due to trauma will significantly impact the national economy. In 1982, approximately sixty-one billion dollars were expended for trauma victims. Decreasing deaths, decreasing patient in-hospital time, and decreasing permanent disabilities from trauma will lower the national economic burden caused by trauma. The present invention can have a significant impact on morbidity and mortality, thereby not only saving lives, but also in returning productive workers to society.

Other objects and features of the present invention will become apparent from the following detailed description in connection with the accompanying drawings.

DETAILED DESCRIPTION OF THE INVENTION

Figure 1:
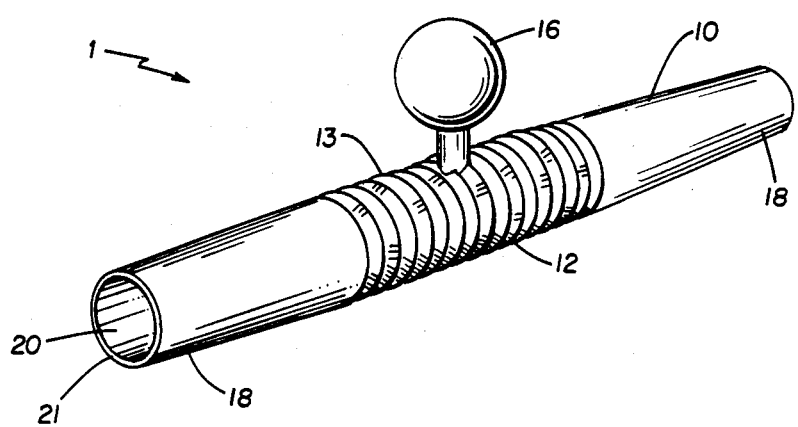
FIG. 1 is a perspective view of one embodiment of the present invention.
Figure 2A:
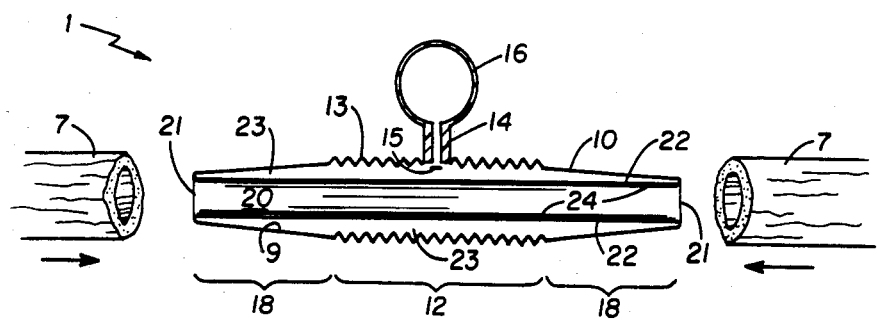
FIG. 2 contains cross-sectional views of the device presented in FIG. 1, in a rest state and in an inflated state.
Figure 2B:
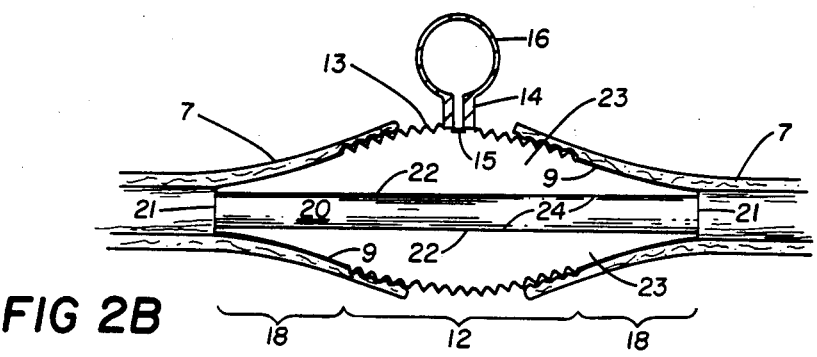
Figure 3:
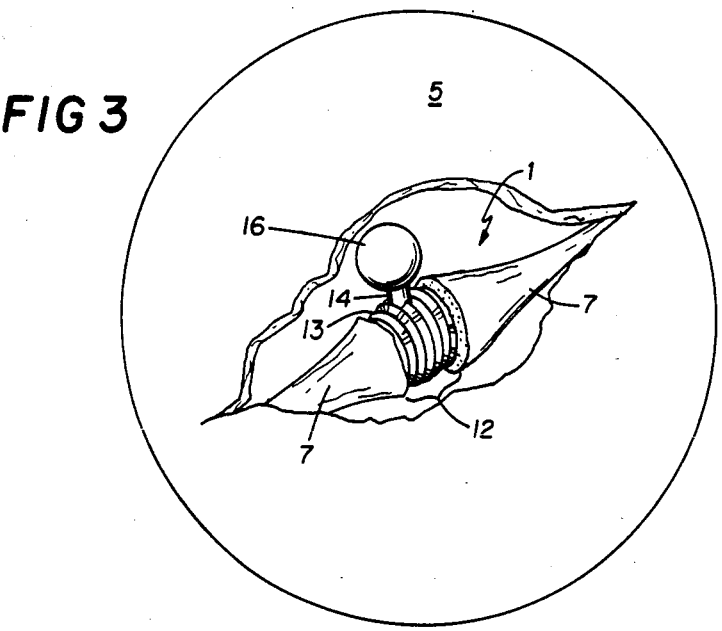
FIG. 3 is a perspective view of the embodiment of FIG. 1 in place in a patient's body.

Referring more particularly to the drawings in detail, wherein like numerals indicate like elements, reference numeral 1 refers generally to the temporary anastomotic device comprising the invention. FIG. 1 is a perspective view of one embodiment of the invention, FIG. 2 contains cross-sectional views of the device 1 in a rest state (FIG. 2A) and in an inflated state (FIG. 2B), and FIG. 3 shows the invention 1 in place in a patient's body 5. The device 1 has a tube-like outer casing 10, the center section 12 of which contains corrugations 13 about its general circumference, and is interconnected by means of a squat tube 14 to a bladder 16. The two end sections 18 of the casing 10 are smooth and gradually taper off toward the device's ends 21. The entire casing 10 is made of flexible material. The center section 12 is particularly expansible. This may be done by means of the corrugations 13, or by making the center section 12 from a more flexible material.

The temporary anastomotic device 1 is constructed with a cylinder 20 concentric within the casing 10. The inner cylinder 20 extends to and is open at both device ends 21. The outer face 22 of the inner cyclinder 20 and the inside face 9 of the casing 10 form an enclosed chamber 23. The chamber 23 is formed around the inner cyclinder 20 and is concentric about said cylinder 20. The chamber 23 may be filled with air, gas or liquid by means of the bladder 16 interconnected to the chamber 23 via the tube 14 fitted through the casing 10. A simple valve 15, open when the bladder 16 is squeezed and closed when the chamber 23 is filled, would prevent seepage from the chamber 23 back into the bladder 16. The inner cylinder 20 is made of a material stiffer than that of the casing 10, so that it will not be subject to collapse or kinking when the chamber 23 is inflated. As air, gas or liquid is pumped into the chamber 23, the center section 12 of the casing 10 expands. Since it is envisioned that the device 1 would be a throw away item, discarded after one use, refilling the bladder 16 after usage would not be a consideration.

Before the chamber 23 is expanded, the end sections 18 of the device 1 are inserted into the damaged blood vessel 7. The device 1 is so inserted that each end of the damaged blood vessel 7 is drawn over the device corrugations 13. As the chamber 23 is pumped by the bladder 16, the expanding casing 10 becomes snugly fitted within the blood vessel 7. The device corrugations 13 assist expansion and tend to prevent the blood vessel from sliding off the device 1. Since the inside wall 24 of the inner cyclinder 20 is made of a material harder than that of the outer casing 10, the cylinder 20 will hold its shape, allowing blood flow through it and thereby through the damaged blood vessel 7. External patches or clips may be temporarily applied over the entire area to hold the anastomotic device 1 in place. The snug fit of the device 1 within the blood vessel 7 will tend to halt bleeding from the blood vessel 7 to the surrounding area 5.

Even though the device 1 is designed as a temporary measure, blood clotting due to the damage to the blood vessel 7 and due to the insertion of a foreign device 1 is a real danger. To reduce this danger, the inside wall 24 of the inner cylinder 20 would be very smooth. The inside wall 24 may also be coated with a medication, e.g., possibly an anti-coagulant. Where there is extensive wall damage to the blood vessel 7, extensions to the device's end sections 18 may be required.

Figure 4A:
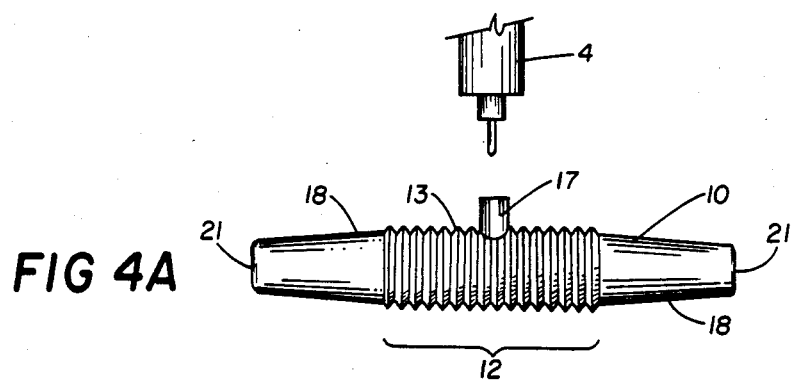
FIG. 4 contains side elevational and cross-sectional views of the invention, disclosing an alternative embodiment.
Figure 4B:
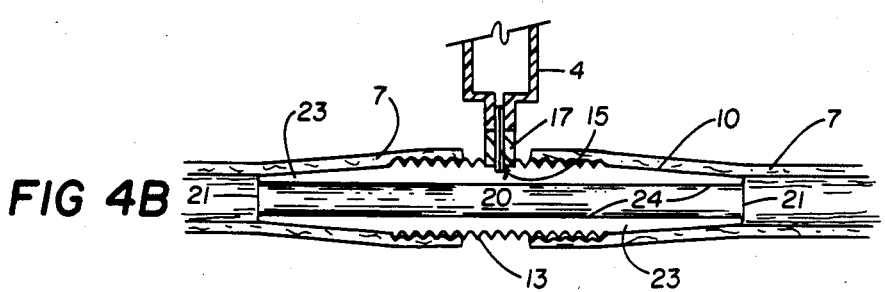
Figure 5A:
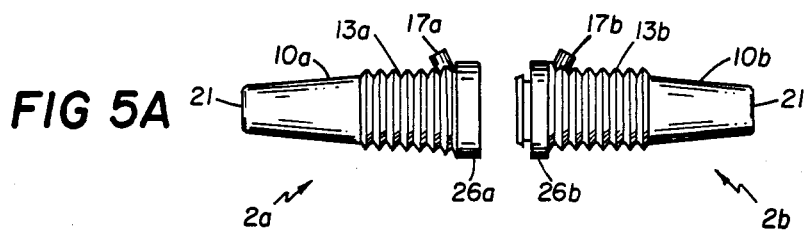
FIG. 5 contains side elevational and cross-sectional views similar to FIG. 4 revealing another alternative embodiment.
Figure 5B:
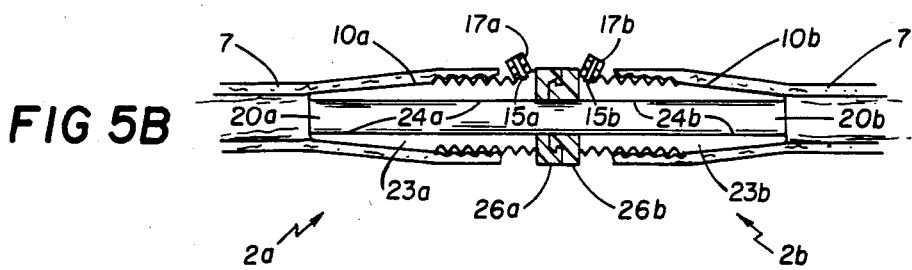

FIG. 4 and FIG. 5 illustrate two alternative embodiments of the invention 1 in side elevational view (FIG. 4A and FIG. 5A), and in cross-sectional view (FIG. 4B and FIG. 5B). In FIG. 4, the bladder 16 of FIGS. 1, 2, and 3 has been replaced with an inflating tube 17. In the embodiment shown in FIG. 4, the internal chamber 23 is inflated with air, gas or liquid by means of a hypodermic syringe 4, external to the casing 10, inserted through the inflating tube 17 interconnecting the syringe 4 with the chamber 23 internal to the casing 10. A simple valve 15 could also be used in this embodiment to close off the chamber 23 when expanded. FIG. 5 presents an embodiment of the invention in which the temporary anastomotic device 1 comes in two sections 2a and 2b. Construction is similar to the above embodiments with some differences. Each section 2a and 2b has its own casing 10a and 10b, inner cylinder 20a and 20b, and inner chamber 23a and 23b. Air, gas or liquid is inserted with a hypodermic syringe 4 through inflating tubes 17a and 17b in each section 2a and 2b. The sections 2a and 2b are interconnected by conventionally designed snap or screw locks 26a and 26b, one section 2a typically having a female connector receptacle 26a, and the other section 2b typically having a male connector receptacle 26b.

It is understood that the above-described embodiments are merely illustrative of the application. Other embodiments may be readily devised by those skilled in the art which will embody the principles of the invention and fall within the spirit and scope thereof.

I claim:

1. An anastomotic device for temporarily rejoining and reforming damaged blood vessels, comprising:
    a flexible, tubular casing, made of expansible material, having an inner and an outer face, a center section and two end sections, the center section being made of a material more expansible than that of the two end sections and said center section containing corrugations about its general circumference, and the two end sections of said tubular casing being smooth about their general circumference;
    a cylinder having two ends and an inner and outer face, not subject to collapse or kinking, concentrically positioned within the casing, extending to and open at both ends of the casing, and so joined to the casing as to form an enclosed chamber around and between the outer face of the cylinder and the inner face of the casing; and
    means for introducing an inflating substance into said enclosed chamber.

2. An anastomotic device for temporarily rejoining and reforming damaged blood vessels, comprising:
    a flexible, tubular casing, made of expansible material, having an inner and an outer face, a center section, two end sections, the center section being made of a material more expansible then that of the two end sections and said center section containing corrugations about its general circumference, and the two end sections of which are smooth about their general circumference;
    a cylinder having two ends and an inner and outer face, not subject to collapse or kinking, concentrically positioned within the casing, extending to and open at both ends of the casing, and so joined to the casing as to form an enclosed chamber around and between the outer face of the cylinder and the inner face of the casing; and
    means for introducing an inflating substance into said enclosed chamber, said means being comprised of a bladder external to the casing, and a tube interconnecting the bladder through the casing to the enclosed chamber.

3. An anastomic device as described in claim 2 further comprising:
    a valve attached to the tube at the enclosed chamber so that when the bladder is squeezed, the valve is in an open position, and when the chamber is filled, the valve is in a closed position.

* * * * *